United States Patent [19]

Wissmann et al.

[11] 4,331,592
[45] May 25, 1982

[54] PROCESS FOR THE PREPARATION OF CARBOXYLIC ACID AMIDES AND PEPTIDES

[75] Inventors: Hans Wissmann, Bad Soden am Taunus; Hans-Jerg Kleiner, Kronberg am Taunus, both of Fed. Rep. of Germany

[73] Assignee: Hoechst Aktiengesellschaft, Frankfurt am Main, Fed. Rep. of Germany

[21] Appl. No.: 112,458

[22] Filed: Jan. 16, 1980

[30] Foreign Application Priority Data

Jan. 18, 1979 [DE] Fed. Rep. of Germany ....... 2901843

[51] Int. Cl.$^3$ .................. C07C 103/52; C07C 125/06
[52] U.S. Cl. ............................. 260/112.5 R; 560/27; 549/72; 564/138; 564/139; 564/140; 564/141; 260/558; 548/365
[58] Field of Search ..................... 260/112.5 R, 558 P; 560/27; 546/379; 549/72; 564/138, 139, 140, 141

[56] References Cited

U.S. PATENT DOCUMENTS

| | | | |
|---|---|---|---|
| 1,938,902 | 12/1963 | Grether et al. | 564/140 |
| 1,972,142 | 9/1934 | Goldstein | 260/124 |
| 2,691,010 | 10/1954 | Anderson | 564/139 |
| 3,630,875 | 12/1971 | Kuffer | 260/502.4 R |
| 4,043,991 | 8/1977 | Hamma et al. | 260/112.5 R |
| 4,128,542 | 12/1978 | Atherton et al. | 260/112.5 R |

FOREIGN PATENT DOCUMENTS

| | | |
|---|---|---|
| 2730524 | 1/1978 | Fed. Rep. of Germany . |
| 714427 | 10/1954 | United Kingdom . |
| 1374900 | 11/1974 | United Kingdom . |
| 1410339 | 10/1975 | United Kingdom . |
| 1410440 | 10/1975 | United Kingdom . |

OTHER PUBLICATIONS

Kosolapoff, "Organophosphorus Compounds", p. 4, (1965).
"The Chemistry of Amides", 1970, pp. 104–109.
"The Peptides", vol. I, pp. 75–77.
Roberts et al., "Basic Principles of Organic Chemistry", W. A. Benjamin Inc., New York, 1965, pp. 1198–1200.
Grimmel et al., J. Am. Chem. Soc. 68, 539–542, (1946).
Mueller, "Methoden der Organischen Chemie", vol. XII, Part 1, Georg Thieme Verlag, Stuttgart, 1963, pp. 610–611.
Cherbuliez et al., Helv. Chim. Acta. 44, 1193–2260, (1961).
Kosolapoff et al., "Organic Phosphorus Compounds", vol. 6, Wiley-Interscience, New York, 1973, pp. 4–5.
Kosolapoff et al., "Organic Phosphorus Compounds", vol. 7, Wiley-Interscience, 1976, pp. iii and 6.
Mueller, "Methoden der Organischen Chemie", vol. XV, Part 2, Georg Thieme Verlag, Stuttgart, 1974, pp. 246–250.
Mueller, "Methoden der Organischen Chemie", vol. XV, Part 2, Georg Thieme Verlag, Stuttgart, 1974, pp. 226–230.
Chem. Abstr. 53, 244 i, (1959).
Cope et al. (Eds.), "Organic Reactions", vol. 12, John Wiley & Sons, New York, 1962, pp. 262–278.
Jackson et al., Tetrahedron Letters 40, 3627–3630, (1976).

*Primary Examiner*—Delbert R. Phillips
*Attorney, Agent, or Firm*—Curtis, Morris & Safford

[57] ABSTRACT

What is disclosed is a method of making a carboxylic acid amide, including a peptide, by reacting a compound having a free amino group with a compound having a free carboxy group in the presence of an anhydride of an alkane-phosphonic acid.

3 Claims, No Drawings

PROCESS FOR THE PREPARATION OF CARBOXYLIC ACID AMIDES AND PEPTIDES

The present invention relates to a method for the preparation of carboxylic acid amides and peptides, which comprises reacting compounds containing a free amino group with compounds which contain free carboxyl groups in the presence of anhydrides of alkane-phosphonic acids.

The process of the invention is suitable both for the preparation of carboxylic acid amides and especially for the preparation of peptides.

Suitable carboxylic acid amides are, above all, amides of aromatic, aliphatic and heterocyclic carboxylic acids, for example benzoic acids, naphthoic acids or anthracene acids which may be substituted by alkyl, alkoxy, nitro, dialkylamino, acylamino or nitrile groups, furthermore phenylalkylcarboxylic acids with linear or branched alkyl radicals of up to 10 carbon atoms, which may contain the above-mentioned substituents at the benzene nucleus, and in addition N- or S-containing heterocyclic carboxylic acids with 5- and 6-membered rings which may also carry the above mentioned substituents.

As amino components for the preparation of the carboxylic acid amides there may be mentioned, besides ammonia, also aliphatic, aromatic or heterocyclically substituted primary and secondary amines with the abovementioned substituents.

For the preparation of aminocarboxylic acid amides or peptides, use is made of those aminocarboxylic acid derivatives or peptides whose carboxyl groups are protected, which compounds are reacted with aminocarboxylic acids or peptides containing free carboxyl groups whose amino groups are protected, however. Other functional groups in the amino acids or peptides are suitably protected by the common peptide protective groups; said protective groups may be split off in the usual way following the process of the invention.

When preparing carboxylic acid amides, the temperature used is room temperature or a slightly elevated temperature of 60° C., and aminocarboxylic acid amides or peptides are prepared at a temperature of from −10° to +40° C., preferably a temperature between 0° and room temperature.

Suitable compounds for splitting off water according to the process of the invention are the anhydrides of the linear or branched, optionally cyclic, alkanephosphonic acids having a chain length of from 1 to 8 carbon atoms, preferably up to 4 carbon atoms.

As anhydrides of the alkane-phosphonic acids there may be mentioned, for example, methane-phosphonic acid anhydride, ethane-phosphonic acid anhydride, n-propane-phosphonic acid anhydride, and n-butane-phosphonic acid anhydride.

The alkane-phosphonic acid anhydrides may be prepared in known manner, for example, as has been described in Houben-Weyl, Meth. d. Org. Chem. (1963) vol. XII/1, page 612.

For preparing peptides, especially pure alkane-phosphonic acid anhydrides are used. Anhydrides of this kind may be obtained by reacting pure alkane-phosphonic acid dichlorides with 1 mol of water and subsequently eliminating the hydrogen chloride still remaining in the reaction mixture by applying a vacuum. Said anhydrides may also be prepared preferably according to the process of German Offenlegungsschrift No. 2,811,628. In this case pure alkane-phosphonic acids are converted into the anhydrides by splitting off water at high temperatures; a subsequent purification by means of vacuum distillation may be useful.

If peptides are to be synthesized, the reaction according to the invention is carried at advantageously in a neutral or at most slightly alkaline medium.

According to the most simple method, the medium is buffered by adding aliphatic and cycloaliphatic tertiary bases, such as N-methylmorpholine, N-ethylmorpholine or trialkylamines of up to 6 carbon atoms per alkyl radical. The alkane-phosphonic acid anhydrides used according to the invention are in most cases well soluble in solvents, such as dimethyl sulfoxide, DMF, DMA, diethyl phosphite, 1-methyl-pyrrolidone, chloroform and methylene chloride.

For preparing oligopeptides, an amino acid or a peptide with a blocked carboxyl group and an amino acid or a peptide with a blocked amino group are used as starting materials. For the protection of the carboxyl group and the amino group all protective groups that are common in peptide synthesis. For the protection of the carboxyl group there are used, for example, esters of linear and branched aliphatic alcohols, such as methanol, ethanol, and tert. butanol, are used cf. Houben-Weyl, Methoden d. Org. Chemie vol. 15/1 (1974) Synthese von Peptiden, pages 315 to 350. Use may also be made of esters of araliphatic alcohols, such as benzyl alcohol and diphenylmethyl carbinol.

For the protection of the amino groups, for example, the carbobenzoxy radical and the carbo-tert. butyloxy radical may be used, cf. Houben-Weyl, Methoden d. Org. Chemie vol. 15/1 (1974) pages 47 and 117 et seq. As solvents, all anhydrous inert solvents that are common in peptide synthesis, for example methylene chloride, chloroform, dimethyl formamide, dimethyl acetamide, dioxan, diethyl phosphite, 1-methylpyrrolidone, and tetrahydrofuran may be used.

The alkane-phosphonic acid anhydrides of the invention are preferably used in an excess amount (from 2 to 2.5 mols of alkane-phosphonic acid anhydride per mol of peptide bond to be obtained).

The process of the invention involves considerable advantages.

No allergenic effect has been observed so far with the acids which comprise the basis of the synthesis reagent. The toxicity is insignificant. The reagent itself, which can be prepared in a simple manner, does not yield any sparingly soluble by-products following the synthesis, especially when using distilled alkane-phosphonic acid anhydrides. Such by-products are obtained, for example, in the commonly-used peptide bonding reaction employing dicyclohexyl carbodiimide.

As compared with the processes for peptide synthesis described so far, which use activating agents based on 3- or 5-valent phosphorus, for example the peptide syntheses according to the phosphorazo method [Liebigs Ann. Chem. 580, p. 68 (1953)], the synthesis methods using diethyl chlorophosphite and tetraethyl pyrophosphite [J. Am. Chem. Soc. 74, 5304, 5307 and 5309 (1952)] and the synthesis method using polyphosphoric acid esters [Ber. 91, (1958) pp. 1073 to 1082 or J. org. Chem. 26, 2534 (1961)], the process of the invention shows the advantage of a lower degree of racemization with the common use of amino acid- or peptide ester hydrochlorides.

Thus, for example, Z-Phe-Gly-OEt prepared according to the process of the invention shows an $[\alpha]_D$ value of $-17°$ (c=2, ethanol). The method using diethyl chlorophosphite [J. Am. Chem. Soc. 74, 5307 (1952)] yields a peptide with $[\alpha]_D$ of $-16°$ (c=2, ethanol). The Z-Asp (OBu$^t$)-Phe-NH$_2$ described in Example 4 shows an $[\alpha]_D$ of $-33.8°$ (c=1, ethanol) as compared with the literature value of $-30.7°$ [phosphorazo method, Hoppe-Seyler's Z. Physiol. Chem. 353, 1250 (1972)]. The synthesis of Z-Gly-Phe-Gly-OEt [J. Am. Chem. Soc. 80, 2902 (1958)], known as a test for racemization, gave the L-compound in a yield of 75% of theory when using the method of the invention, cf. Example 10. Portions that were sparingly soluble in ethanol (DL-peptides) were not obtained. On the other hand, in the synthesis of the tripeptide with polyphosphoric acid ethyl esters according to J. Org. Chem. 26, 2534 (1961), 32% of DL-compounds sparingly soluble in ethanol and 32% of L-compound are obtained.

Another advantage of the process of the invention resides in the high thermal stability of the synthesis reagent. As compared with the polyphosphoric acid esters, a further advantage is to be seen above all in the distillability of the alkane-phosphonic acid anhydrides, which makes it possible to obtain defined oligomers.

The strong solubilizing effect of the alkane-phosphonic acid anhydrides and the secondary products thereof in the course of the peptide synthesis is also very desirable, especially in the synthesis of longer peptide chains and sparingly soluble peptide sequences.

The products of the invention are employed as intermediates or for the preparation of pharmaceutically active peptides.

The following Examples illustrate the invention. Unless otherwise indicated, the concentration in percent means percent by weight.

EXAMPLE 1

Carbobenzoxy-glycylglycine-ethyl ester

At 0° C., 7.0 g (0.05 mol) of H-Gly-OC$_2$H$_5$·HCl, 15 ml (0.118 mol) of N-ethyl morpholine and 36 ml of a 55% (W/V) solution of n-propane-phosphonic acid anhydride (0.1 mol) in methylene chloride are added successively to a solution of 10.5 g (0.05 mol) of carbobenzoxy-glycine, while stirring and cooling thoroughly. The mixture is brought to room temperature, while stirring. After 16 hours of standing at room temperature, the solvent is distilled off in vacuo and the residue is dissolved in a mixture of 200 ml of ethyl acetate and 100 ml of 5% potassium bisulfate solution. The ethyl acetate solution is washed twice with 100 ml each of saturated sodium bicarbonate solution, dried over sodium sulfate and evaporated in vacuo.

Yield: 11.8 g of Z-dipeptide ester having a melting point of 81° (80% of the th.), after recrystallization from ethyl acetate/petroleum ether: 82°

EXAMPLE 2

Z-Val-Tyr(Bu$^t$)His-OCH$_3$

At 0° C., 30 ml of N-ethyl morpholine, 21.5 g of Z-Val-Tyr-OH and 40 ml of a 38% solution of n-propane-phosphonic acid anhydride in methylene chloride having a temperature of up to 10° C. are added successively, while stirring, to a suspension of 11.5 g of H-His-OCH$_3$·HCl in 100 ml of dimethyl formamide. The reaction solution, which is practically clear after the exothermic reaction has been completed, is allowed to stand overnight at room temperature. Thereafter the solvents are evaporated in vacuo at room temperature and a mixture of 100 ml of saturated NaHCO$_3$ solution and 200 ml of acetic acid ethyl ester is added to the residue. The crude product is introduced into the ethyl acetate phase, while shaking, which phase is washed with a small amount of water, dried over sodium sulfate and then brought to dryness in vacuo. The Z-tripeptide ester remaining in the residue becomes solid upon digesting with diethyl ether.

Yield: 20 g, melting point 188° to 190° $[\alpha]_D = -8.2°$ (c=1, DMF). Another 3.5 g of the peptide may be obtained from the mother liquor by evaporating the solvent and recrystallizing the mixture from acetic acid ethyl ester/diethyl ether. Total yield: 76% of the theory.

EXAMPLE 3

Z-Pro-Ala-Lys-(Boc)-Phe-NH$_2$ 19.1 Grams of H—Lys(Boc)—Phe—NH$_2$·HCl (0.044 mol) are dissolved in 100 ml of dimethyl formamide and, at 0° C. 26 ml of N-ethyl morpholine, 16.0 g (0.005 mol) of Z-Pro-Ala-OH and 22 g of n-propane-phosphonic acid anhydride in the form of a 38% (W/V) solution in methylene chloride are added, while stirring. The reaction mixture is allowed to stand at room temperature for 48 hours, after which it is brought to dryness in vacuo at room temperature. The residue is digested with 100 ml of 2 N sodium carbonate solution, 100 ml of 10% aqueous citric acid solution and 100 ml of dist. water and is then dried in vacuo over phosphorus pentoxide.

Yield: 30.1 g=87% of the th. $[\alpha]_D = -27.0°$ (c=1, DMF); melt. point 163° C.

EXAMPLE 4

Z—Asp(OBu$^t$)—Phe—NH$_2$

At 0° C., 1.6 g (0.01 mol) of H—Phe—NH$_2$ are dissolved, together with 28 ml (0.22 mol) of N-ethyl morpholine, in 20 ml of dimethyl formamide. While stirring and cooling, 3.23 g (0.01 mol) of Z-Asp(OBu$^t$)OH and 11.4 ml of 38% n-propane-phosphonic acid anhydride solution in methylene chloride are added to said solution. The reaction solution thus prepared is allowed to stand overnight at room temperature. After removing the solvent by distillation and adding water, the product is extracted with ethyl acetate, washed with water, aqueous sodium bicarbonate solution, and with a 5% aqueous KHSO$_4$ solution. Then, the ethyl acetate solution is dried over sodium sulfate and concentrated and the final product is precipitated with diethyl ether.

Yield: 4.0 g (85% of the th.), m.p. 162° $[\alpha]_D = -33.1°$ (c=1, CH$_3$OH)

EXAMPLE 5

Boc-Met-Gly-OEt

At 0° C., 24.8 g of Boc-Met-OH, 14.0 g of H-Gly-OEt·HCl, 60 ml of N-ethyl morpholine and 67 ml of a 67% methylene chloride solution of n-propane-phosphonic acid anhydride are added successively to 115 ml of dimethyl formamide, with stirring and the exclusion of moisture. Stirring is continued at room temperature for another 20 hours. Then the solvents are removed by distillation in vacuo at room temperature and water is added to the residue. The precipitated peptide ester is dissolved in ethyl acetate and the ethyl acetate solution is washed successively with saturated aqueous NaHCO$_3$ solution, 5% KHSO$_4$ solution and water. The acyl peptide ester is obtained in a crystalline form from the ethyl acetate solution, dried over sodium sulfate, after the solvent has been largely removed by evaporation in vacuo at room temperature. The product is washed with a small amount of absolute diethyl ether and is filtered off with suction.

Yield after drying in vacuo over $P_2O_5$:29.5 g=93% of theory, m.p. 53° C., $[\alpha]_D = -15.4°$ (c=1, DMF)

EXAMPLE 6

Boc-Tyr(Etoc)-Met-Gly-$OC_2H_5$

23 Grams of H—Met—Gly—$OC_2H_5$·HCl are dissolved in 200 ml of dimethyl formamide, and 58 ml of N-ethyl morpholine, 31.5 g of Boc-Tyr(Etoc)-OH and 44 g of n-propane-phosphonic acid anhydride dissolved in 60 ml of methylene chloride are added at 0° C. with intense cooling. The solution is allowed to stand for 20 hours at room temperature. Then the solvents are distilled off in vacuo at room temperature and the reaction mixture is worked up as has been described in Example 5.

Yield: 40.7 g (84% of theory)
m.p. 137.5° $[\alpha]_D = -11.7°$ (c=1, DMF)

EXAMPLE 7

Z—Gly-Thr(Bu$^t$)Phe—$OCH_3$ 18.6 Grams (0.05 mol) of H—Thr(Bu$^t$)—Phe—$OCH_3$·HCl, 30 ml (0.238 mol) of N-ethyl morpholine and 10.4 g (0.05 mol) of Z-Gly-OH are dissolved successively in 120 ml of dimethyl sulfoxide (p.a. Merck), and 16.3 g of methanephosphonic acid annydride are added portionwise, while stirring, while cooling with ice and with the exclusion of moisture. The methane-phosphonic acid anhydride is slowly dissolved. Stirring is continued for another 24 hours at room temperature and the reaction solution is then introduced into 500 ml of saturated sodium bicarbonate solution, whereupon the reaction product precipitates. The supernatant solution is decanted and the precipitate is dissolved in acetic acid ethyl ester. The ethyl acetate solution is washed with water, dried over magnesium sulfate, largely concentrated in vacuo, and the final product is precipitated with petroleum ether. It crystallizes overnight at +4° C.

EXAMPLE 8

Z—Phe—cyclohexylamide

30 Grams (0.01 mol) of Z—Phe—OH, 1.0 g (0.01 mol; 1.2 ml) of cyclohexylamine and 5 ml of N-ethyl morpholine are dissolved in 30 ml of DMF and while cooling with ice, 8.8 g of a 50% by weight n-propane-phosphonic acid anhydride solution (0.0435 mol) in methylene chloride are added. When the exothermic reaction has been completed (with a rise in temperature of up to +10°), the solution is allowed to reach room temperature, while stirring, and the reaction mixture is then worked up as has been described in Example 1.

Yield: 3.1 g (81% of the th.) $[\alpha]_D = -2.8°$ (c=1, DMF) m.p. 167° C.

EXAMPLE 9

Z—Ala—Tyr—Gly—Leu—Arg—Pro—Gly—$NH_2$

A mixture of 4.99 g (0.01 mol) of Z—Ala—Tyr—Gly—OH, 5.13 g (0.01 mol) of H—Leu—Arg—Pro—Gly—$NH_2$·2 HCl, 20 ml of dimethyl formamide and 10 ml (0.078 mol) of N-ethyl morpholine is cooled to −10° C., while stirring and with the exclusion of moisture. Subsequently 6.6 g (0.022 mol) of n-hexane-phosphonic acid anhydride as a 50% solution in methylene chloride (p.a., dist. over $P_2O_5$) are added dropwise, with additional stirring. During the addition, the temperature is not to exceed +10° C. The resulting solution is continued to be stirred for another 3 hours and is then allowed to stand overnight. Subsequently it is concentrated in high vacuum at room temperature to about 30 ml, 100 ml of saturated sodium bicarbonate solution are added, and the mixture is extracted three times with a total of 400 ml of ethyl acetate. Said ethyl acetate solution is then extracted twice with 50 ml each of saturated sodium bicarbonate solution and water, and the product is dried over sodium sulfate and isolated by evaporating the ethyl acetate solution in vacuo, whereupon the residue is triturated with absolute diethyl ether.

Yield: 7.46 g (81% of the th.) m.p. 130° (decomp.) $[\alpha]_D = -29.2°$ (c=1, DMF)

PREPARATION OF THE N-HEXANE-PHOSPHONIC ACID ANHYDRIDE

In a glass flask provided with a 12 cm Vigreux column still mounted on top and with a connected air condenser with receiver, 200 g of n-hexane-phosphonic acid are heated to a maximum of 340° C. at a pressure of about 0.3 mmHg. At a transition temperature of from 225° to 250° C., hexane-phosphonic acid anhydride is distilled off in the course of 10 hours. About 22 g of water are condensed in a cooling trap connected in series with the apparatus. 170 g of the anhydride are obtained. The product is again fractionated prior to the reaction. It gives a clear solution in methylene chloride, chloroform, dimethyl formamide, dimethyl sulfoxide, petroleum ether of a boiling point of from 40° to 80° C., ether, toluene, dioxan, cyclohexane and tetrahydrofuran.

EXAMPLE 10

Z—Gly—Phe—Gly—OEt 1.4 Grams (0.01 mol) of H-Gly-OEt·HCl and 3.56 g (0.01 mol) of Z-Gly-Phe-OH are suspended, while stirring, in 30 ml of dimethyl formamide. After cooling to −5° C., 5.6 ml (0.044 mol) of N-ethyl morpholine are added with stirring and the exclusion of moisture. With further stirring and cooling, 8.8 g of a 50% methylene chloride solution of n-propane-phosphonic acid anhydride (0.021 mol) are added dropwise. In the course of this process the temperature of the reaction mixture is not to exceed +10° C. Subsequently stirring is continued for another hour and the mixture is allowed to stand for 48 hours at room temperature. The solvents are distilled off in high vacuum and 50 ml of ice water are added. After crystallization, the precipitated final product is filtered off with suction, washed with sodium bicarbonate solution, citric acid solution (5% strength) and water and is dried over $P_2O_5$ in vacuo.

Yield: 4.30 g (98% of the th.) $[\alpha]_D = -11.9°$ (c=2, ethanol) m.p. 119° C.

EXAMPLE 11

1-Phenyl-2,3-dimethyl-4-(4-oxyphenyl-propionylamino)-pyrazolone(5)

88 Grams of a 50% solution of propane-phosphonic acid anhydride in methylene chloride are added dropwise to a solution of 16.6 g (0.1 mol) of p-oxyphenyl-propionic acid, 21 g (0.1 mol) of 1-phenyl-2,3-dimethyl- 4-aminopyrazolone(5) and 68 ml of N-ethyl morpholine, the solution being stirred with the exclusion of moisture. The temperature is maintained at a level below +40° C., if necessary, by reducing the feed of propanephosphonic acid anhydride. Stirring is continued for another 6 hours, and the mixture is then allowed to stand at room temperature for 24 hours. Thereafter the reaction solution is diluted with 800 ml of methylene chloride and is then washed three times with 50 ml each of 5% potassium bisulfate solution, saturated sodium bicarbonate solution and water.

The product is dried over magnesium sulfate. It crystallizes upon concentrating the dried methylene chloride solution in vacuo at room temperature. A smaller residual fraction may also be obtained from the filtrate precipitated with petroleum ether.

Total yield: 25.0 g=70% of the th., m.p. 218°.

EXAMPLE 12

Benzoic acid-β-phenylethylamide 17.6 Grams of a 50% solution of n-propane-phosphonic acid anhydride in methylene chloride are added in 3 portions, with stirring and the exclusion of moisture, to a solution of 2.4 g of β-phenylethylamine, 2.2 g of benzoic acid and 14 ml of N-ethyl morpholine in 25 ml of methylene chloride. The temperature rises to about +40° C. The mixture is cooled to room temperature, while stirring, and is worked up after 24 hours of standing by adding 350 ml of methylene chloride and extracting the solution three times with 50 ml each of water, saturated sodium carbonate solution and potassium bisulfate solution. The crude product crystallizes from the methylene chloride solution dried over magnesium sulfate. Said product is filtered off with suction together with a small amount of petroleum ether (boiling point 40° to 60° C.).

Yield: 3.8 g=84% of the th.

m.p. 111° to 112° C., after recrystallization from ethanol:

116° C. (lamellae)

EXAMPLE 13

Thiophene-2-carboxylic acid-β-phenylethylamide

In a manner analogous to that of Example 12, thiophene-2-carboxylic acid-β-phenylethylamide is obtained from 2.6 g of thiophene-2-carboxylic acid, 2.4 g of β-phenylethylamine, 14 ml of N-ethyl morpholine dissolved in 15 ml of methylene chloride and 17.6 g of a 50% solution of propane-phosphonic acid anhydride in methylene chloride.

Yield: 3.5 g=76% of theory.

m.p. 108° to 109° C., after recrystallization from ethnol: 111°

EXAMPLE 14

Benzoic acid-4-nitroanilide

A total of 17.6 g of a 50% solution of n-propanephosphonic acid anhydride are added in 3 portions, with stirring and cooling, to a mixture of 2.8 g of 4-nitroaniline, 15.5 ml of triethylamine, 2.2 g of benzoic acid and 15 ml of methylene chloride. The mixture is continued to be stirred for another hour at room temperature, while becoming clear over this period. After standing for 32 hours at room temperature, said mixture is worked up as has been described in Example 1.

Yield after recrystallization from ethanol: 3.38 g=70% of the th.

m.p. 198° C.

What is claimed is:

1. The method of making a carboxylic acid amide which comprises reacting a compound having a free amino group with a compound having a free carboxyl group in the presence of an anhydride of an alkane phosphonic acid.

2. A method as in claim 1 wherein said carboxylic acid amide is a peptide.

3. A method as in claim 1 wherein the alkane group in said alkane phosphonic acid has from 1 to 8 carbon atoms.

* * * * *